(12) United States Patent
Sivaraja et al.

(10) Patent No.: US 6,183,956 B1
(45) Date of Patent: Feb. 6, 2001

(54) HIGH THROUGHPUT IN VITRO SCREENING ASSAYS FOR TRANSCRIPTION MODULATORS

(75) Inventors: Mohanram Sivaraja, Palo Alto, CA (US); Berta Strulovici, Lower Gwynedd, PA (US); Osvaldo A. Flores, Redwood City, CA (US)

(73) Assignee: Tularik, Incorporated, So. San Francisco, CA (US)

( * ) Notice: Under 35 U.S.C. 154(b), the term of this patent shall be extended for 0 days.

(21) Appl. No.: 09/052,995

(22) Filed: Mar. 31, 1998

(51) Int. Cl.$^7$ ....................................................... C12Q 1/68

(52) U.S. Cl. ............................... 435/6; 435/69.1; 436/501

(58) Field of Search ............................... 435/6, 810, 69.1; 436/501; 935/77, 78

(56) References Cited

U.S. PATENT DOCUMENTS

| | | | |
|---|---|---|---|
| 4,833,084 | 5/1989 | Carrico | 435/240.27 |
| 5,591,586 * | 1/1997 | Lewis | 435/6 |
| 5,612,458 | 3/1997 | Hyldig-Nielsen et al. | 530/388.21 |
| 5,741,673 * | 4/1998 | Montminy et al. | 435/69.1 |

FOREIGN PATENT DOCUMENTS

| | | | |
|---|---|---|---|
| 2129163 | 1/1996 | (CA) | C12P/21/08 |
| WO 95/33051 | 12/1995 | (WO) | C12N/15/12 |
| WO 97/14812 | 4/1997 | (WO) | C12Q/1/68 |

OTHER PUBLICATIONS

Schiffman, "HPV Testing Helps Reduce Fasle–Positive Pap Smear Interpretations", *CB. Gyn. News*, p. 10 (Jul. 1993).

Clinical Lab Products, p. 30 (Oct. 1992).

Burton W. Blais, "Transcriptional Enhancement of the *Listeria monocytogenes* PCR and Simple Immunoenzymatic Assay of the Product Using Anti–RNA:DNA Antibodies", *Applied and Environmental Microbiology*, p. 348–352 (1994).

Fliss et al., "Production and Characterization of Anti–DNA–RNA Monoclonal Antibodies and Their Application in Listeria Detectiion", *Applied and Environmental Microbiology*, p. 2698–2705 (1993).

Fliss et al., "Anti–DNA . RNA antibodies: an efficient tool for non–isotopic detection of Listeria species through a liquid–phase hybridization assay", *Appl. Microbiol Biotechnol* 43:717–724 (1995).

Miller et al., "Detection of Bacteria by Hybridization of rRNA and DNA–Latex and Immunodetection of Hybrids", *Journal of Clinical Microbiology*, p. 1271–1276 (1988).

Newman et al., "Solution hybridization and enzyme Immunoassay for biotinylated DNA–RNA hybrids to detect enteroviral RNA in cell culture", *Molecular and Cellular Probes* 3:375–382, (1989).

Casebolt et al., "Monoclonal Antibody Solution Hybridization Assay for Detection of Mouse Hepatitis Virus Infection", *Journal of Clinical Microbiology*. p. 608–612 (1992).

Engler–Blum et al., "Reduction of Background Problems in Nonradioactive Northern and Southern Blot Analyses Enables Higher Sensitivity Than $^{32}$P–Based Hybridizations", *Medical University Clinic*, Department 3, p. 235–244 (1992).

(List continued on next page.)

*Primary Examiner*—Ardin H. Marschel
(74) *Attorney, Agent, or Firm*—Townsend and Townsend and Crew LLP

(57) ABSTRACT

High-throughput in vitro assays are provided for identifying modulators of transcription activity and RNA expression. New assays, related compositions, apparatus and integrated systems are provided.

38 Claims, 6 Drawing Sheets

OTHER PUBLICATIONS

Coutlee et al., "Nonisotopic Detection of RNA in an Enzyme Immunoassay Using a Monoclonal Antibody against DNA–RNA Hybrids", *Analtical Biochemistry* 181:153–162 (1989).

Viscidi et al., "Monoclonal Antibody Solution Hybridization Assay for Detection of Human Immunodeficiency Virus Nucleic Acids", *Journal of Clinical Microbiology*, 27:1 120–125 (1989).

Ishii et al., Bead–Based Sandwich Hybridization Characteristics of Oligonucleotide–Alkaline Phosphatase Conjugates and Their Potential for Quantitating Target RNA Sequences, *Bioconjugates Chem.* 4:1 34–41 (1993).

Pisetsky et al., "Binding Specificity of a Monoclonal Anti–DNA Antibody", *Molecular Immunology* 19:5 645–650 (1992).

Ballard et al., "Monoclonal Murine Anti–Nuleic Acid Antibody with Double–Stranded Specificity", *Molecular Immunology* 19:6 793–799 (1982).

Stollar et al., "Immunochemical Measurement of Double–Stranded RNA of Unifected and Arbovirus–Infected Mammalian Cells", *Proceeding of the National Academy of Sciences*, 65:4 993–1000 (1970).

High resolution detection of DNA–RNA hybirds in situ by indirect immunofluorescence, *Nature* 265:472–473 (1977).

Prooijen–Knegt et al., "In Situ Hybridization of DNA Sequences in Human Metaphase Chromosomes Visualized by an Indirect Fluorescent Immunocytochemical Procedure", *Exp Cell Res* 141:397–407 (1982).

Boguslawski et al., "Characterization on monoclonal antibody to DNA . RNA and its application to immunodetection of hybrids", *Journal of Immunological Methods* 89:123–130 (1996).

Fisher et al., "A Novel Cyclin Asociates with MO15/CDK7 to Form the CDK–Activating Kinas", *Cell.* Vol. 78:713–724 (1994).

Matthews et al., Analytical Biochemistry, vol. 169, pp. 1–25, 1988.*

Instruction Manual Digene Hybrid Capture™ Systems, (1995).

Digene Hybrid Capture™ System, MPV DNA Assay(1992).

* cited by examiner

HIGH THROUGHPUT IN VITRO SCREENING ASSAYS FOR TRANSCRIPTION MODULATORS

CROSS REFERENCE TO RELATED APPLICATIONS

This application is related to the patent application entitled "High throughput assays for detection of mRNA in cells," Ser. No. 09/052,841 filed Mar. 31, 1998, herein incorporated by reference.

FIELD OF THE INVENTION

The field of the invention relates to high-throughput in vitro assays for identifying modulators of transcription activity and RNA expression in solid phase assays. New assays, related compositions, apparatus and integrated systems are provided.

BACKGROUND OF THE INVENTION

Gene regulatory processes are fundamental in most, if not all, forms of disease, as well as in all of developmental biology. Accordingly, a primary goal of modern medicine is to understand gene regulation and to identify specific modulators of gene expression. These modulators serve as antineoplastic agents, antiviral agents, antifungal agents, and the like, for the treatment of a very wide variety of diseases.

Assays for monitoring gene expression are well known, including northern blotting, RT-PCR, RNase and S1 protection, reporter gene expression (e.g., chloramphenicol transferase (CAT) assays), etc. General texts that describe assays for monitoring gene expression include Sambrook et al., *Molecular Cloning—A Laboratory Manual* (2nd ed.), Vol. 1–3, Cold Spring Harbor Laboratory, Cold Spring Harbor, New York, 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1997) ("Ausubel"). Specialized apparatuses for performing these assays are commercially available.

In addition to these standard methods typically used to monitor gene expression, specialized formats for detection of nucleic acids are also available. For example, Coutlee et al. (1989) *Analytical Biochemistry* 181:153–162 describe non-isotopic detection of RNA in an enzyme immunoassay using a monoclonal antibody which binds DNA:RNA hybrids. In these assays, hybridization of an RNA target with a biotinylated DNA probe is performed, followed by incubation of the hybridized target-probe duplex on an antibiotin plate, reaction of the resulting bound duplex with a β-galactosidase labeled monoclonal antibody specific for RNA-DNA hybrids, and addition of a fluorescent substrate. In another example, a "sandwich" hybridization method is described for non-isotopic detection of RNA using oligonucleotides (Ishii & Ghosh (1993) *Bioconjugate Chem.* 4:34–41). In these assays, the RNA target is hybridized to a first complementary oligonucleotide, which is linked to a bead. The RNA target is then hybridized to a second complementary oligonucleotide conjugated to alkaline phosphatase. The RNA target is detected by providing a chemiluminescent alkaline phosphatase substrate.

Other investigators have also reported immunological detection of DNA:RNA hybrids, including Bogulavski et al. (1986) *J. Immunol. Methods* 89:123–130; Prooijen-Knegt (1982) *Exp. Cell Res.* 141:397–407; Rudkin (1976) *Nature* 265:472–473, and Stollar (1970) *PNAS* 65:993–1000. Similarly, detection of DNA:DNA hybrids and RNA:RNA hybrids has also been described. See, Ballard (1982) *Mol. Immunol.* 19:793–799; Pisetsky and Caster (1982) *Mol. Immunol.* 19:645–650, and Stollar (1970) *PNAS* 65:993–1000. Stollar (1970) and Rudkin (1976) (both supra) showed that DNA:RNA hybrids in solution can be captured on plastic or nitrocellulose supports coated with an anti-poly (A)-poly(dT) polyclonal antibody. A monoclonal antibody against DNA:RNA heteroduplexes and RNA:RNA hybrids, which does not recognize DNA duplexes, single-stranded DNA or single-stranded RNA, has been prepared and characterized. See, e.g., Bogulavski et al. (1986) *J. Immunol. Methods* 89:123–130; Viscidi et al. (1988) *J. Clin. Microbiol.* 41:199–209, and Kiney et al. (1989) *J. Clin. Microbiol.* 27:6–12. This antibody was used for the detection of DNA:RNA hybrids immobilized by binding of the DNA component of the duplex to a nylon bead, or to avidin latex. Immunoassays for detecting nucleic acids have been adapted to in vitro qualitative detection of human papillomavirus (HPV), e.g., for use in detecting cervical abnormalities. Kits comprising antibodies specific for DNA:RNA hybrids are available, e.g., from Digene Diagnostics, Inc. (Beltsville, Md.).

One strategy for identifying pharmaceutical lead compounds is to develop an assay that provides appropriate conditions for monitoring the activity of a therapeutic target for a particular disease. This assay is then used to screen large numbers of potential modulators of the therapeutic target in the assay. For example, libraries of chemical compounds can be screened in solid phase assays using robotic components. Although the immunoassay-based and sandwich-based nucleic acid detection strategies described above have been useful for detecting DNAs, RNAs, and DNA:RNA hybrids, they have not been adapted to high throughput gene expression monitoring assays that could be used for screening for pharmaceutical lead compounds. Such high throughput assays for expression monitoring and pharmaceutical compound screening are desirable. This invention provides these assays, as well as other features which will become apparent upon review.

SUMMARY OF THE INVENTION

High throughput in vitro assays for detecting modulators of RNA expression are provided. Inhibitors and activators of RNA expression can be screened using such assays, as can modulators that alter transcriptional activation. Solid phase high throughput assays are provided, as are related assay compositions, integrated systems for assay screening, and other features that will be evident upon review.

In one aspect, high throughput in vitro RNA detection assays are provided. The selected RNA in the sample is contacted with oligonucleotides that are complementary to the selected RNA. Single-stranded RNA in the sample is cleaved, typically with RNases such as RNase A. The sample is then incubated with a recognition agent that binds to RNA duplexes. The recognition agent is detected either directly or indirectly, indicating the level of expression of the selected RNA.

In another aspect, high throughput in vitro expression assays are provided. In such assays, the transcription mixtures contain an expression cassette with a promoter operably linked to a DNA encoding a selected G-less or A-less RNA. The single-stranded RNA in the sample is cleaved at guanine residues, typically by RNase T1, or at adenine residues, typically by RNase U2. The sample is then incubated with a recognition reagent that captures the RNA. The selected RNA is then detected either directly or indirectly, indicating the level of expression of the selected RNA.

In one embodiment, the selected RNA is transcribed from an expression cassette with a promoter operably linked to a DNA encoding a selected RNA. In one embodiment, expression of the selected RNA is induced by providing a transcriptional activating molecule that induces transcription of the DNA encoding the selected RNA. In another embodiment, the sample is treated with a compound suspected of having the ability to modulate expression or transcription activation of the selected RNA. In another embodiment, the recognition reagent is an antibody that binds to DNA:RNA duplexes. In another embodiment, a second recognition reagent is used to detect the selected RNA.

Kits, compositions, and integrated systems for performing the assays are also provided.

DEFINITIONS

Figure 1:
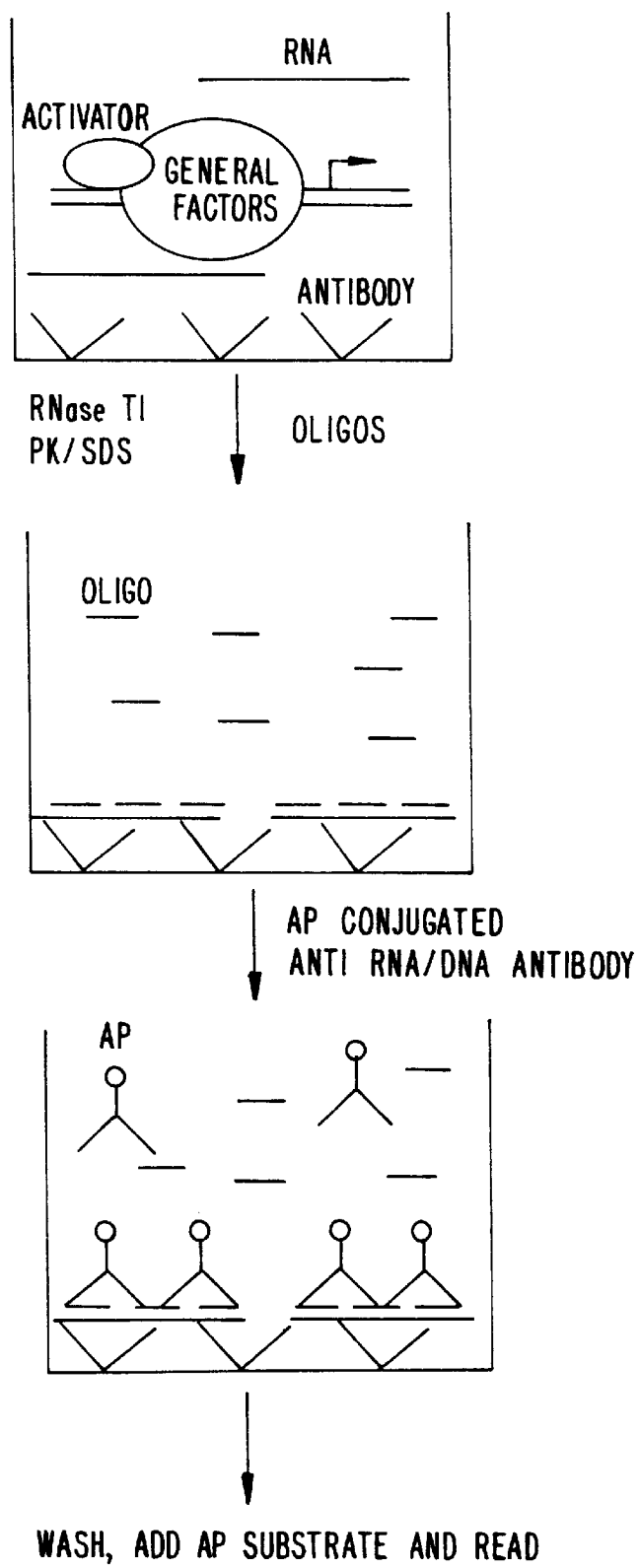
FIG. 1 is a drawing of a solid phase assay of the invention using an anti-RNA:DNA antibody to capture and detect the selected RNA.

The following terms are expressly defined for purposes of this application.

A "ribonucleic acid" or "RNA" is a polymer comprising ribonucleotide monomer units. The polymer can be a naturally occurring ribonucleotide polymer such as mRNA, rRNA or tRNA. The polymer optionally comprises non-naturally occurring nucleotides, e.g., synthetic monomer units in the polymer chain. The RNA can be single or double stranded. A "region" of the RNA is any sequence or subsequence of the RNA, including the full-length of the RNA.

A "G-less" or an "A-less" RNA refers to an RNA molecule that lacks guanine residues or adenine residues in a region of the RNA, including the full-length of the RNA. Guanine residue analogues recognized by RNase T1 (which cleaves RNA at guanine positions) are also excluded from G-less RNA. Adenine residue analogues recognized by RNase U2 (which cleaves RNA at adenine positions) are also excluded from A-less RNA.

An "RNA duplex" is a double stranded nucleic acid comprising at least one RNA strand. The duplex can be an RNA:RNA strand, an RNA:DNA strand (also referred to as an DNA:RNA hybrid or DNA:RNA heteroduplex) or can comprise a strand comprising artificial nucleotides. An RNA homoduplex is a base-paired double-stranded RNA. An RNA heteroduplex comprises an RNA strand and a strand comprising DNA nucleotide monomers. All or a region of the duplex may be double stranded. Typically, at least 15 bases of the duplex will be double-stranded. Preferably, 30–50 bases of the duplex will be double-stranded.

A "recognition reagent" is a reagent that is directly or indirectly detectable and that binds, directly or indirectly, to the indicated molecule (e.g., RNA duplex, homoduplex or heteroduplex). A typical recognition reagent in the context of the invention is an antibody that specifically binds nucleic acid duplexes or an oligonucleotide that specifically hybridizes to a selected RNA. Optionally, the recognition reagent is immobilized on a solid support.

A "detectable moiety" or "label" is a composition detectable, either directly or indirectly, by spectroscopic, photochemical, biochemical, immunochemical, or chemical means. For example, useful labels include $^{32}P$, fluorescent dyes, electron-dense reagents, enzymes and their substrates (e.g., as commonly used in enzyme-linked immunoassays, e.g., alkaline phosphatase and horse radish peroxidase), biotin-streptavidin, digoxigenin, or haptens and proteins for which antisera or monoclonal antibodies are available. The label or detectable moiety is typically bound, either covalently, through a linker or chemical bound, or through ionic, van der Waals or hydrogen bonds to the molecule to be detected.

A "transcriptional activating" molecule is a molecule that stimulates or induces transcription of a selected RNA under specified conditions, e.g., in a cell or in vitro.

A "modulator of transcription activity" is a compound that increases or decreases transcription of a coding DNA in a selected system. A "potential modulator of transcription" is a compound that is to be assessed for the ability to increase or decrease transcription of a coding DNA in a selected system. A "modulator of RNA expression" is a compound which increases or decreases the level of RNA in a selected system. A "potential modulator of RNA expression" is a compound that is to be assessed for the ability to increase or decrease the level of RNA in a selected system. The level of RNA in the cell can be a result of promoter control, signal transduction systems regulating transcription and transcription factors, splicing of nuclear RNA into mRNA, RNA degradation pathways, RNA termination and polyadenylation, and the like. Samples or assays that are treated with a potential modulator are compared to control samples without the test compound, to examine the extent of inhibition or activation of transcription, or the extent or inhibition or activation of expression. Control samples (untreated with test inhibitors or activators) are assigned a relative transcription or expression activity value of 100. Inhibition of transcription or expression is achieved when the transcription or expression activity value of the test sample relative to the control is about 75, preferably 50, more preferably 25. Activation is achieved when the transcription or expression activity value of the test sample relative to the control is about 150, more preferably 200.

"Chaotropic agent" refers to a molecule that denatures proteins, such as guanidine isothiocyanate or a detergent.

"Transcription" refers to the process by which an RNA molecule is polymerized using a coding DNA template that encodes the RNA.

"Expression" refers to the relative level of an RNA in a cell, which is the result of transcription, splicing, RNA polyadenylation, degradation, and the like.

A "coding DNA molecule" is a DNA molecule that encodes an RNA molecule. The coding DNA molecule will typically comprise a promoter operably linked to a sequence that, when transcribed, provides a selected RNA.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

The phrase "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

"In vitro" refers to assays that do not require the presence of a cell with an intact cellular membrane.

DETAILED DESCRIPTION OF THE INVENTION

I. Introduction

High throughput methods, compositions, kits, and integrated systems for detecting RNA levels in vitro and the effect of potential modulators of RNA levels are provided. Accordingly, the assays of the invention provide at least two immediately useful properties. First, the assays can be used to detect RNA levels in vitro, serving as a replacement for standard molecular tools such as northern analysis, in situ hybridization, RT-PCR, and the like. Thus, the assays provide broadly applicable tools for assessing gene expression in a high-throughput format.

Second, the assays provide for the identification of modulators of RNA expression levels. These modulators are valuable for in vitro modification of signal transduction, transcription, splicing, RNA degradation, and the like, e.g., as tools for recombinant methods, cell culture modulators, etc. More importantly, these modulators provide lead compounds for drug development for a variety of conditions, including as antibacterial, antifungal, antiviral, antineoplastic, inflammation modulatory, or immune system modulatory agents. Accordingly, the assays are of immediate value for their ability to identify lead compounds for pharmaceutical or other applications. The assays are particularly well suited to high throughput automation, making them especially valuable for their ability to identify lead compounds.

Indeed, because RNA expression is fundamental in all biological processes, including cell division, growth, replication, differentiation, repair, infection of cells, etc., modulators identified by the assays of the invention are leads for a variety of conditions, including neoplasia, inflammation, allergic hypersensitivity, metabolic disease, genetic disease, viral infection, bacterial infection, fungal infection, or the like. In addition, transcription modulators, which specifically target critical genes in undesired organisms such as viruses, fungi, agricultural pests, or the like, can serve as fungicides, bactericides, herbicides, insecticides, and the like. Thus, the range of conditions that RNA expression modulators are applicable to includes conditions in humans and other animals, and in plants, e.g., for agricultural applications.

Automation of in vitro based assays for the high throughput screening assays of the invention is facilitated by consideration of desired assay parameters. First, it is desirable to have high enough sensitivity to detect as little as either: as little as approximately 50–500 atomoles of mRNA using the DNA:RNA antibody capture in vitro reaction (see FIG. 5), or as little as approximately 5–10 femtomoles of mRNA using the sandwich hybridization method and capture with steptavidin beads (see FIG. 6). It will be appreciated that many prior art assays for detecting rare RNAs rely upon RT-PCR amplification of rare mRNA to enhance the amount of corresponding nucleic acid (RT-PCR provides many DNA copies of the mRNA for detection and analysis) present in the in vitro reaction. PCR can result in loss of quantitation and adds additional steps to the assay, such as thermocycler steps. PCR also leads to loss of fidelity. Second, the assay should be as simple as possible, with a minimum number of manipulations and relatively short incubations, to facilitate robotic automation of the assay. Third, the assay should be general in format so that it can be used to monitor the expression of essentially any RNA without needing to substantially change the format of the assay to adapt it to monitoring a particular selected RNA or modulator. Fourth, the assay should be inexpensive to perform, as high-throughput formats can provide thousands of separate assays per day, making cost an important consideration for development of high-throughput assays. The assays of the invention meet these design parameters.

Further in this regard, several aspects of the discovery were surprising. First, the assay can be performed in a very short time frame relative to other polynucleotide assay formats which detect RNA expression; an entire assay can be performed in under about three hours. Second, the assay is extremely sensitive relative to previously described formats and requires only minimal quantities of the necessary reagents and does not require expansion of the RNA to be detected (prior art methods often rely on RT-PCR to expand RNA for detection). Third, because of the high sensitivity and short incubation times of the assays, it is very economical to run the assays in an automated high-throughput format. Finally, the assays are very robust, with insignificant variation seen between control reactions, minimizing the need for repetitive control and calibration steps.

II. In vitro RNA detection assays and assays for potential modulators

In one aspect, the invention provides methods of detecting a selected RNA in vitro. In the methods, a sample having the selected RNA is contacted with an oligonucleotide, which has a region complementary to the selected RNA. The oligonucleotide forms an RNA duplex with a region of the selected RNA. Single-stranded RNA in the cell is cleaved to reduce background in subsequent assay steps. The RNA duplex is then detected by contacting the RNA duplex with a recognition reagent, such as an antibody, which binds RNA homo or hetero duplexes. The recognition reagent is directly or indirectly detectable, and is typically bound to a solid support. Optionally, a second recognition reagent can be used, which is typically not bound to a solid support.

In another aspect, the invention provides methods of detecting a selected G-less or A-less RNA in vitro. In the methods, a sample having an expression cassette with a promoter operably linked to a nucleic acid encoding a G-less or an A-less RNA is incubated in a transcription reaction. The single-stranded RNA in the reaction is then cleaved at guanine or adenine positions. The sample is further incubated with a recognition reagent immobilized on a solid substrate, where the recognition agent binds to the G-less or A-less RNA. The level of the G-less or A-less RNA in the sample is then detected. These methods is broadly applicable to the detection of RNA levels that result from transcription and processing of the RNA.

Indeed, it will be appreciated that the assays described herein can be used to detect the presence or absence of an RNA. This feature is particularly useful in the context of screening for potential modulators of RNA transcription or expression. It will be appreciated that the goal of many modulator screening protocols is to identify modulators that block expression of an RNA, which would otherwise be expressed. In such a case, the absence of a selected RNA following modulator incubation may be a goal of the assay. Similarly, in other instances, an increase in RNA expression may be a goal of the screening protocol using the assay. In either case, it can be desirable to screen for specific modulators, i.e., modulators which increase or decrease the level of a selected RNA such as a pathogenic RNA, but which have no effect on the level of expression of other RNAs.

Accordingly, in one aspect, the invention provides methods of measuring expression of a selected RNA in the presence of a potential nucleic acid transcription activity modulator in vitro. In the methods, a sample, typically a transcription reaction comprising a DNA encoding the selected RNA, is incubated in the presence of a potential transcription activity modulator. The sample can also comprises lysed cells, which have been previously contacted with a trancriptional or expression activator to induce expression of the selected RNA. In one aspect, an oligonucleotide is introduced into the reaction. The oligonucleotide comprises a region complementary to a region of the selected RNA. Typically, single-stranded RNA is cleaved in the sample to eliminate background problems. In another aspect, the selected RNA is a G-less or an A-less RNA and the single-stranded RNA in the reaction is cleaved at guanine or adenine residues. The sample is then incubated with a recognition reagent. In one aspect, the recognition reagent binds to RNA duplexes (e.g., an anti-RNA duplex antibody). In another aspect, the recognition reagent binds to G-less or A-less RNA. The recognition reagent is directly or indirectly detectable and the level of expression of the selected RNA is determined by detecting the amount of recognition reagent bound to the selected RNA in the sample.

Where desired, the assay can be refined by the use of positive or negative controls, and/or by comparison to the results observed for other RNAs. For example, a "positive" control assay will utilize a modulator that is known to increase the expression of a selected RNA (e.g., a hormone for a hormone responsive promoter, Tat for a Tat responsive promoter, etc.). Such positive controls are used to infer that the components of the assay are functioning properly. A negative control can include a modulator known to decrease expression of a particular RNA, such as α-amanitin, which decreases transcription from pol II promoters. Such negative controls can be used to determine base-line background signal levels in the assay. Comparison of the results of multiple assays can be used to find modulators that are specific for a single selected RNA, or for a single type of organism. For example, the effects of a modulator on expression of a selected RNA from a gene comprising a human promoter can be compared to the effects observed from a bacterial promoter, to find modulators that selectively modulate expression of the bacterial promoter. This a desirable feature, e.g., where the assay is used in a screening protocol to identify anti-bacterial agents.

A. Selected RNA

The selected RNA to be detected in the assays of the present invention is expressed from any of a variety of operably linked transcription elements. The operably linked transcriptional elements can be from a native gene, e.g., an gene that is endogenously expressed in a cell or that is recombinant, or a heterologous nucleic acid, e.g., a promoter from a therapeutic target operably linked to a reporter nucleic acid. Transcription of the selected nucleic acid can be induced by addition of a direct or indirect transcriptional activating molecule, or basal levels of transcription can be measured. A modulator is optionally added, optionally in conjunction with a transcriptional activating molecule.

As is evident to one of skill in the art, the selected RNA can be any of a large number of RNAs. As described above, the selected RNA can be a reporter RNA operably linked to a native or heterologous promoter of choice. Examples of selected RNAs that are standardized and easily detectable (e.g., in reporter constructs), referred to as "reporter RNAs," include A-less and G-less RNAs, Il-8 RNA, and other RNAs that have features allowing easy detection. Optionally, the expression from the promoter of choice is induced by transcriptional or expression activating factors. Many transcriptional and expression activating factors act in a cascade, e.g., they induce expression of a first tier of genes, which gene products subsequently induce the expression of a second tier of genes. Transcriptional and expression activating factors, as described below, therefore also may serve as selected RNAs in the assays of the invention.

B. Expression and transcriptional activators

Transcription of the selected nucleic acid can be induced by addition of a direct or indirect transcriptional activator, or basal levels of transcription can be measured. A modulator is optionally added to the assays of the invention, optionally in conjunction with a transcriptional activator.

The transcriptional requirements for a number of genes are known, making it possible to induce expression of a wide variety of RNAs using available techniques. For example, hormones, cytokines, chemicals, ions (e.g., $Ca^{++}$) or the like can be incubated with an in vitro transcription reaction to induce transcription of a variety of genes. Similarly, a reaction can contain genes expressed from a selected pathogen (virus, bacteria, spore, protozoa, or the like) or pathogenic gene or protein (e.g., that encode Tat or Rev from HIV), which typically induces transcription of selected cellular or pathogenic organism genes. Because these pathogenic agents often express RNAs encoded in the pathogenic genome, these pathogenic RNAs can be detected using the assays herein.

Example transcriptional and expression activators, that may be added to the transcription reaction (or which are themselves expressed as selected RNAs), include genes and proteins that modulate cell growth, differentiation, regulation, or the like. Expression and transcriptional activators are found in prokaryotes, viruses, and eukaryotes, including fungi, plants, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA. Expression activators include cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, and corticosterone. Preferred targets include the LDL receptor, heat shock proteins, and uncoupling proteins, e.g., UCP2 and UCP3.

Similarly, the activators of gene expression or selected genes expressed in infectious organisms can be detected, including infectious fungi, e.g., Aspergillus, Candida species; bacteria, particularly *E. coli*, which serves a model for pathogenic bacteria, as well as medically important bacteria such as Staphylococci (e.g., *aureus*), Streptococci (e.g., *pneumoniae*), Clostridia (e.g., *perfringens*), Neisseria (e.g., *gonorrhoea*), Enterobacteriaceae (e.g., *coli*), Helicobacter (e.g., *pylori*), Vibrio (e.g., *cholerae*), Capylobacter (e.g., *jejuni*), Pseudomonas (e.g., *aeruginosa*), Haemophilus (e.g., *influenzae*), Bordetella (e.g., *pertussis*), Mycoplasma (e.g., *pneumoniae*), Ureaplasma (e.g., *urealyticum*), Legionella (e.g., *pneumophila*), Spirochetes (e.g., Treponema, Leptospira, and Borrelia), Mycobacteria (e.g., *tuberculosis, smegmatis*), Actinomyces (e.g., *israelii*), Nocardia (e.g., *asteroides*), Chlamydia (e.g., *trachomatis*), Rickettsia, Coxiella, Ehrlichia, Rochalimaea, Brucella, Yersinia, Fracisella, and Pasteurella; protozoa such as sporozoa (e.g., Plasmodia), rhizopods (e.g., Entamoeba) and flagellates (Trypanosoma, Leishmania, Trichomonas, Giardia, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (examples include Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., especially HIV and HTLV, and certain DNA to RNA viruses such as Hepatitis B virus. Other assays are designed to be relevant to non-medical uses, such as assays for inhibitors of transcription in crop pests e.g., insects, fungi, weed plants, and the like.

C. Coding DNAs

Coding DNAs that encode selected RNAs are optionally derived from a natural source or can be recombinant. The DNAs can be recombinant DNAs, e.g., plasmids comprising a promoter of interest linked to a reporter sequence, or an expressed nucleic acid linked to a heterologous, well-understood promoter. It will be appreciated that either configuration can be desirable, depending on the application. For example, the assay for a reporter RNA can be optimized for use with particular oligonucleotides, facilitating development of assays which detect expression of the RNA from any selected promoter. Similarly, a well-understood promoter can be used to direct expression of a variety of RNAs to test for effects of modulators on RNA stability, splicing or the like.

A wide variety of molecular and biochemical methods are available for making coding DNAs. Examples of appropriate molecular techniques for generating recombinant nucleic acids, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); as well as in Sambrook, and Ausubel (both supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., Applied Biosystems (Foster City, Calif.), Digene Diagnostics, Inc. (Beltsville, Md.) as well as many other commercial sources known to one of skill.

D. Oligonucleotide synthesis and selection

In the assays of the invention, oligonucleotides are used to bind to selected RNAs to form RNA duplexes, or are used as recognition reagents. Most commonly, these nucleic acids are DNA or RNA oligonucleotides that are made synthetically. Synthetic oligonucleotides are typically synthesized chemically according to common solid phase phosphoramidite triester methods described, e.g., by Beaucage & Caruthers (1981) *Tetrahedron Letts.* 22(20):1859–1862, e.g., using an automated synthesizer, as described in Needham-VanDevanter et al. (1984) *Nucleic Acids Res.* 12:6159–6168. Oligonucleotides can also be custom made and ordered from a variety of commercial sources known to persons of skill. In other embodiments, the nucleic acids are made recombinantly according to standard techniques, described, e.g., in Berger, Sambrook and Ausubel, all supra.

Oligonucleotides are selected to have particular hybridization characteristics with the selected RNA and to form a duplex with the RNA. Most typically, oligonucleotides are selected to be fully complementary to the selected RNA, although a portion of the oligonucleotide can be non-complementary (e.g., a portion may act as a labeling or cloning element instead of participating in hybridization, or a single oligonucleotide can be used to detect multiple closely related RNAs in separate assays to reduce individual assay costs). The oligonucleotides are preferably selected to have melting temperatures near the temperature of the assay, to enhance hybridization. Such oligonucleotides can be selected using gel-shift assays or programs that analyze predicted RNA secondary structures using, for example, the MFOLD program (Genetics Computer Group, Madison Wis.). However, a surprising aspect of the present invention is the discovery that it is not necessary to perform the assays at high stringency, as background has been determined not to be a problem, even at low or moderate stringency. Without being bound to any particular theory, the step of digesting single-stranded RNA appears to eliminate background binding of the RNA:DNA antibody. The ability to perform the assay at low temperatures (e.g., 37° C.) simplifies automation of the assay, and is, therefore, a desirable feature of the invention.

Accordingly, while it is not necessary to optimize hybridization conditions, it is possible to decrease background in some cases by selecting oligonucleotides and assay conditions so that the oligonucleotide hybridizes to the RNA under stringent conditions, and then performing hybridization steps under stringent conditions. "Stringent hybridization" in the context of these nucleic acid hybridization experiments are sequence dependent, and are different under different environmental parameters. Generally, highly stringent hybridization conditions are selected to be about 5°–15° C. lower than the thermal melting point ($T_m$) for the specific sequence at a defined ionic strength and ph. The $T_m$ is the temperature (under defined ionic strength and pH) at which 50% of the target RNA sequence hybridizes to a perfectly matched oligonucleotide probe. Very stringent conditions are selected to be nearly equal to the $T_m$ for a particular probe (e.g., 0°–5° C. below the melting temperature). It is expected that one of skill is thoroughly familiar with the theory and practice of nucleic acid hybridization and selection of complementary oligonucleotides. See, e.g., Gait (ed.), *Oligonucleotide Synthesis: A Practical Approach,* IRL Press, Oxford (1984); Kuijpers, *Nucleic Acids Research* 18(17):5197 (1994); Dueholm (1994) *J. Org. Chem.* 59:5767–5773; Agrawal (ed.) *Methods in Molecular Biology,* volume 20; and Tijssen (1993) *Laboratory Techniques in biochemistry and molecular biology—hybridization with nucleic acid probes,* e.g., part I chapter 2 "Overview of principles of hybridization and the strategy of nucleic acid probe assays," Elsevier, N.Y., provide a basic guide to nucleic acid hybridization.

Most typically, although oligonucleotides may be of any length, they are often between 8 and 100 nucleotides in length, and preferably between about 10 and 35 nucleotides in length, often about 30 nucleotides in length. The oligonucleotides are optionally selected so that there is minimal complementarity between known genes unrelated to the target RNA and the oligonucleotide. The oligonucleotides are optionally selected to reduce secondary structure formation within the primer. Self-complementary oligonucleotides have poor hybridization properties, because the complementary portions of the self hybridize (i.e., form hairpin structures). The oligonucleotides are also selected so that the oligonucleotides do not hybridize to each other, thereby preventing duplex formation of the oligonucleotides in solution, and possible concatenation of the oligonucleotides. Oligonucleotides are optionally selected so that they have roughly the same thermal melting temperature ($T_m$). Oligonucleotides are typically selected to bind to adjacent sites on a selected RNA to protect large regions of the selected RNA to enhance subsequent detection.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector™ program from Kodak, or the MFOLD program (Genetics Computer Group, Madison Wis.). In addition to programs for primer selection, one of skill can easily design simple programs for any of the desired selection steps.

E. Preparation of transcription extracts and reactions

The in vitro assays of the invention are typically performed using lysed cells that have been previously treated with transcriptional activators, transcription extracts or purified transcription components from prokaryotes, and using lysed cells, transcription extracts, purified transcription components, and isolated nuclei from eukaryotes. Preparation of lysed cells, transcription extracts, transcription components, and isolated nuclei are well known to those of skill in the art. For example, preparation of a standard HeLa cell nuclear extract, used for transcription reactions, is described by Dignam et al., *Nuc. Acids. Res.* 11:1475–1489 (1983). This protocol can be used by one of skill in the art to make extracts from any suitable mammalian cell line, e.g., NIH 3T3, BEK, CHO, COS, BHK21, HEK, 293, Vero, and the like. Additional protocols are known to those of skill in the art for preparation of prokaryotic and plant transcription extracts. Prokaryotic, eukaryotic, plant, and mammalian cells are cultured according to standard conditions prior to extract preparation. Culture of mammalian cell lines and cultured cells from tissue or blood samples is well known in the art. Freshney (*Culture of Animal Cells, a Manual of Basic Technique, third edition* Wiley-Liss, New York (1994)) and the references cited therein provides a general guide to the culture of animal cells. Culture of plant cells is described in Payne et al. (1992) *Plant cell and tissue culture in liquid systems* John Wiley & Sons, Inc. New York, New York. Additional information on cell culture, including prokaryotic cell culture, is found in Ausubel, Sambrook and Berger, supra. Cell culture media are described in Atlas and Parks (eds) *The Handbook of Microbiological Media* (1993) CRC Press, Boca Raton, Fla. Additional information is found in commercial literature such as the Life Science Research Cell Culture catalogue (1998) from Sigma-Aldrich, Inc (St Louis, Mo.) and, e.g., the Plant Culture Catalogue and supplement (1997) also from Sigma-Aldrich, Inc (St Louis, Mo.).

Figure 4:
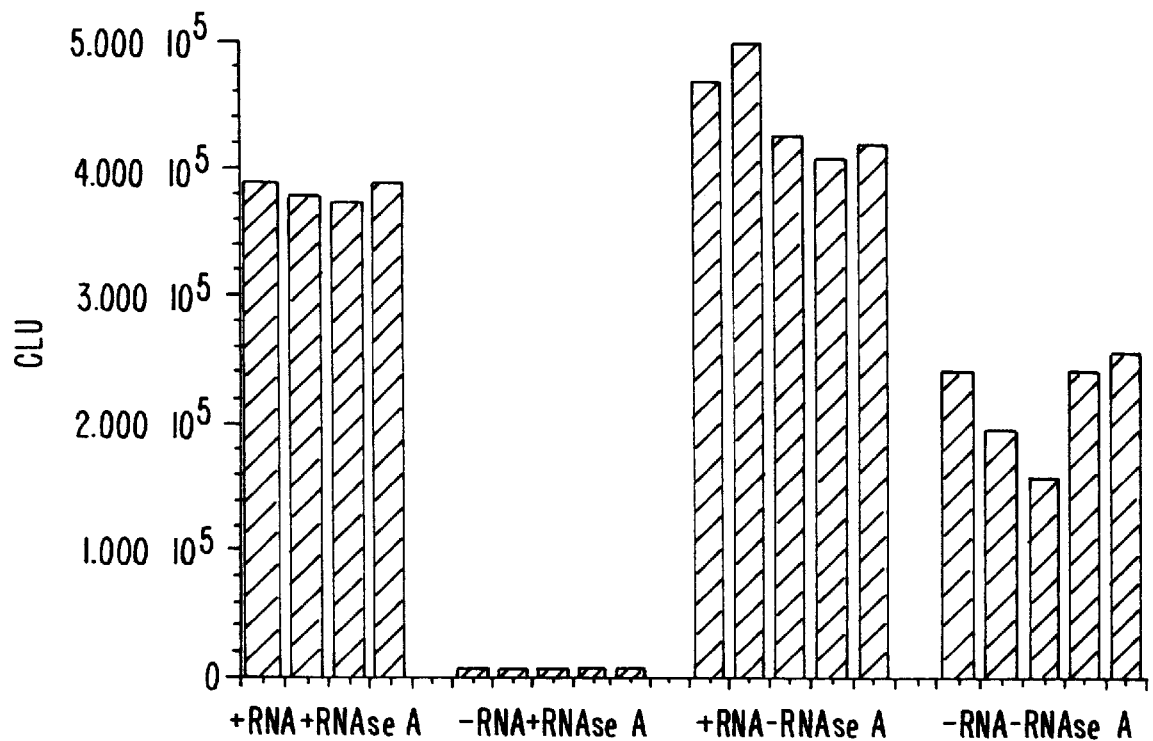
FIG. 4 shows a graph of measurement of IL-8 induction in a cell lysate.

An exemplar assay is shown in FIG. 4. Human endothelial cells were cultured in the presence of IL-1 (which induces IL-8 expression) and lysed. Results are shown for detection of IL-8 RNA with and without RNase A added. The addition of RNase A results in cleavage of single-stranded RNA, while the IL8 RNA-DNA hybrid is protected. This treatment significantly reduced background as measured, e.g., by the signal observed without IL8 oligonucleotides added.

For eukaryotic cells, isolated nuclei can be used for nuclear runoff-type assays. Nuclei can be prepared, e.g., by NP-40 cell lysis, by dounce homogenization, or by cell lysis followed by sucrose gradient centrifugation (see, e.g., Sambrook and Ausubel, both supra). Nuclei can be prepared from, e.g., the cells listed above. Standard reaction conditions are used to promote nascent transcription from the isolated nuclei (see, e.g., Greenberg & Ziff, *Nature* 311:433–438 (1984)). Nuclear runoff assays can be adapted for high throughput procedures by preparing nuclei using, e.g., NP-40 lysis, and then permeablizing and optionally fixing the nuclei to a solid support after transcription (see, e.g., the patent application entitled "High throughput assays for detection of mRNA in cells," Attorney Docket No. 018781-000500, filed Mar. 31, 1998, incorporated herein by reference).

Transcription components, e.g., pol II, can be isolated from both eukaryotic and prokaryotic cells. Transcription factors, as well as transcriptional activators and expression activators, can be isolated and/or cloned and added to the transcription reaction. Components of the eukaryotic pol II holoenzyme include core pol II, a subset of general transcription factors (TFIIE, TFIIF, TFIIH), SRBs (suppressors of mutations in polymerase b), which confer the ability of the pol II holoenzyme to respond to activators, and proteins involved in chromatin remodeling (SWI/SNF) and nucleotide repair. Prokaryotic RNA polymerases have been cloned and are known to those of skill in the art, e.g., T7 RNA polymerase, T3 RNA polymerase, SP6 RNA polymerase, *E. coli* RNA polymerase, etc. In one embodiment, recombinant Tat is added to the transcription reaction (see, e.g., Fisher & Morgan, Cell 78: 713–724 (1994)).

For preparation of lysed cells, the cells are first cultured under standard conditions and then optionally treated with a transcriptional activator. The cells are optionally treated with an expression modulator. The cells are then lysed to examine nascent transcription of the selected RNA. Prokaryote and eukaryote cells are lysed according to standard methods known to those of skill in the art, eg., by contact with a chaotropic agent such as a detergent, or by contacting the cell with a protease, optionally in the presence of a detergent. Preferably, cell lysis occurs under conditions that preserves RNA that has been expressed in the cell. A preferred method of cell lysis uses SDS and proteinase K digestion.

The transcription reactions are incubated according to standard conditions. As described below in Examples I and II, transcription reactions are prepared by incubating nuclei, transcription factors and a coding DNA, or transcriptional extract and a coding DNA, with suitable buffers and ribonucleotide triphosphates (see, e.g., Ausubel and Sambrook, supra). The parameters of the transcription reaction can be varied according to the type of extract, transcriptional activation factors, nuclei, selected RNA, or coding DNA in the reaction. Modulators of transcriptional or expression activity are typically added at the start of the transcription reaction, which is typically incubated for about 1 hour. However, the time of incubation with the modulator and the time of incubation of the reaction is not critical and can be modified according to the particular assay in use.

F. Single-stranded RNA cleavage

In the assays of the invention, single stranded RNA in the reaction is digested to reduce background in the assays. This digestion is performed using an RNase enzyme, or using chemical reagents. Typically, the selected or "reporter" RNA is in a duplex with another nucleic acid, which protects the RNA from degradation by the RNase. Alternatively, the selected RNA lacks a particular nucleotide residue that is recognized by the RNase, e.g., G, A, etc. In such a case the selected RNA is referred to as, e.g., a G-less or an A-less RNA. Suitable RNases are commercially available and known to those of skill in the art. RNases are derived from prokaryotes (e.g., *E. coli* RNase I and III), viruses, and eukaryotes, and have non-specific or specific endonuclease activity. RNases that recognize single-stranded RNA substrates are preferred; however, RNases that recognize double-stranded RNAs (but not, e.g., RNA heteroduplexes) are also useful in the present invention. Examples of suitable RNases include RNase A, which cleaves after pyrimidines; RNase B, a carbohydrate modification of RNase A; RNase S, a proteolytic fragment of RNase A; pancreatic RNase, a mixture of RNase A and B; RNase T1, which cleaves after guanine residues (from *Aspergillus oryzae* or *Ustilago sphaerogena*); RNase T2, which cleaves non-specifically (from *Aspergillus oryzae*); RNase Phy M, which cleaves after adenine and uridine residues (from *Physarum polysephalum*); RNase U2, which cleaves after A residues (from *Ustilago sphaerogena*); *B. cereus* RNase, which cleaves after adenine and cytidine residues; and RNase V1, which cleaves double stranded RNA (from cobra venom). Preferred embodiments include RNase A and RNase T1. Many of these RNase enzymes are commercially available from SIGMA.

After RNase treatment, the assays of the invention optionally include treatment with a protease or a chaotropic reagent, which reduces background and increases signal. Proteases and chaotropic reagents achieve the same result as inactivating proteins, via different mechanisms. Proteases hydrolyze proteins via specific and non-specific proteolytic activity, while chaotropic reagents nonspecifically denature proteins. Suitable proteases are available from prokaryotes, viruses, and eukaryotes. Both proteases and chaotropic agents are commercially available and well known to those skilled in the art. Examples of proteases include proteinase K (from *Tritirachium album*), pronase E (from *Streptomyces griseus*), *Bacillus polymyxa* protease, theromolysin (from thermophilic bacteria), trypsin, subtilisin, furin, and the like. Proteinase K is a preferred embodiment. Examples of chaotropic reagents include detergents, such as Triton X-100 or SDS, or guanidine isothiocyanate, guanidine-HCL, Urea or organic solvents. Chaotropic reagents or proteases are added to the assays after the RNase treatment step, using standard buffer conditions (see, e.g., Example I).

G. Recognition reagents

In the assays of the present invention, recognition reagents are used to bind to RNA homo- or hetero-duplexes, or selected G-less or A-less RNAs. Most commonly, the recognition reagent will be an antibody which recognizes RNA duplexes or an oligonucleotide that hybridizes to a G-less or A-less RNA. Typically, the recognition reagent is immobilized, either directly or indirectly, on a solid support such as a bead, a membrane, or a plate. For example, an antibody that recognizes RNA:DNA duplexes can be immobilized on a plate, thereby capturing the selected RNA. The recognition reagent can also be, e.g., an oligonucleotide that is conjugated to a molecule such as a biotin moiety, which has the ability to bind a second molecule, e.g., a streptavidin molecule, bound to a solid support. Such an oligonucleotide would be complementary to a region of the selected RNA. The recognition reagent is directly or indirectly detectable, and optionally a second recognition reagent is used, which is also detectable either directly or indirectly. In one embodiment, the first recognition reagent is an anti-RNA:DNA antibody, and the second recognition reagent is an anti-RNA:DNA antibody conjugated to an alkaline phosphatase enzyme. In another embodiment, the first recognition reagent is a biotinylated oligonucleotide bound to a streptavidin-bead, and the second recognition reagent is an oligonucleotide labeled, e.g., with a radioactive label.

As discussed above, Coutlee et al. (1989) *Analytical Biochemistry* 181:153–162; Bogulavski et al. (1986) *J. Immunol. Methods* 89:123–130; Prooijen-Knegt (1982) *Exp. Cell Res.* 141:397–407; Rudkin (1976) *Nature* 265:472–473, Stollar (1970) *PNAS* 65:993–1000; Ballard (1982) *Mol. Immunol.* 19:793–799; Pisetsky and Caster (1982) *Mol. Immunol.* 19:645–650; Viscidi et al. (1988) *J. Clin. Microbial.* 41:199–209, and Kiney et al. (1989) *J. Clin. Microbiol.* 27:6–12 describe antibodies to RNA duplexes, including homo and heteroduplexes. Kits comprising antibodies specific for DNA:RNA hybrids are available, e.g., from Digene Diagnostics, Inc. (Beltsville, Md.). Accordingly, such antibodies are commercially available.

In addition to available antibodies, one of skill can easily make antibodies specific for RNA duplexes using existing techniques, or modify those antibodies which are commercially or publicly available. In addition to the art referenced above, general methods of producing polyclonal and monoclonal antibodies are known to those of skill in the art. See, e.g., Paul (ed) (1993) *Fundamental Immunology, Third Edition* Raven Press, Ltd., New York Coligan (1991) *Current Protocols in Immunology* Wiley/Greene, New York; Harlow and Lane (1989) *Antibodies: A Laboratory Manual* Cold Spring Harbor Press, New York; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256:495–497. Other suitable techniques for antibody preparation include selection of libraries of recombinant antibodies in phage or similar vectors. See, Huse et al. (1989) *Science* 246:1275–1281; and Ward et al. (1989) *Nature* 341:544–546. Specific monoclonal and polyclonal antibodies and antisera will usually bind with a $K_D$ of at least about 0.1 $\mu$M, preferably at least about 0.01 $\mu$M or better, and most typically and preferably, 0.001 $\mu$M or better.

As used herein, an "antibody" refers to a protein consisting of one or more polypeptide substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$ a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, New York (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

Indeed, the RNA duplex binding site from an antibody can be fused by recombinant methods to non-immunoglobulin protein sequences to form a recognition reagent which binds to an RNA duplex. An "RNA duplex-binding site" or "binding portion" with reference to an antibody or antibody fusion molecule refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target RNA. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

As used herein, the terms "immunological binding" and "immunological binding properties" refer to the non-covalent interactions of the type which occur between a recognition reagent and an RNA duplex for which the reagent is specific. The strength or affinity of binding interactions can be expressed in terms of the dissociation constant ($K_d$) of the interaction, wherein a smaller $K_d$ represents a greater affinity. Binding properties of selected reagents can be quantified using methods well known in the art. One such method entails measuring the rates of RNA duplex-recognition reagent complex formation and dissociation, wherein those rates depend on the concentrations of the complex partners, the affinity of the interaction, and on parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant $K_d$. See, generally, Davies et al. *Ann. Rev. Biochem.*, 59: 439–473 (1990).

It will be appreciated that molecules other than immunoglobulins and derivatives also make appropriate recognition reagents, and can be made by one of skill. In general, molecules which recognize RNA duplexes (and which, preferably, do not recognize DNA homoduplexes) are suitable. Molecules which bind RNA duplexes include antibodies, nucleic acid binding proteins, nucleic acids and the like. As described above, oligonucleotides are suitable recognition reagents, in particular when the selected RNA is a G-less or an A-less RNA. Additional appropriate reagents can be identified, e.g., by screening available combinatorial chemical (e.g., peptide) libraries to find library members which preferentially bind RNA duplexes.

The recognition reagents are either directly labeled, i.e., comprise or react to produce a detectable label, or are indirectly labeled, i.e., bind to a molecule comprising or reacting to produce a detectable label. Labels can be directly attached to or incorporated into the recognition reagent by chemical or recombinant methods.

In one embodiment, a label is coupled to a molecule, such as an oligonucleotide or an antibody comprising the RNA duplex recognition domain, through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence comprising a proline such as Gly(x)-Pro-Gly(x) (SEQ ID NO:1) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

As described, recognition reagents of the invention are optionally made via recombinant ligation of nucleic acids encoding the constituent parts of the encoded fusion protein (e.g., RNA recognition domain, linker and a label such as a phosphatase, peroxidase or other enzyme) and expression of the resulting construct. Instructions sufficient to direct one of skill through such cloning exercises are found in Sambrook, Berger and Ausubel, all supra, and again, many appropriate recognition reagents, including reagents comprising label domains, are available.

H. Labeling strategies

The detectable labels in the present invention, which are attached to the recognition reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, 2nd ed., Springer Verlag, New York and in Haugland (1996) *Handbook of Fluorescent Probes and Research Chemicals,* a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the recognition reagent acid) according to methods well known in the art. As indicated above, a wide variety of labels may be used, with the choice of label depending on sensitivity required, ease of conjugation with the compound, stability requirements, available instrumentation, and disposal provisions.

In general, a detector which monitors a particular probe or probe combination is used to detect the recognition reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling nucleic acids is digitized for subsequent computer analysis.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

One preferred example of detectable secondary labeling strategies uses an antibody that recognizes RNA duplexes linked to an enzyme (typically by recombinant or covalent chemical bonding). The antibody is detected when the enzyme reacts with its substrate, producing a detectable product. In another preferred example, the enzyme or protein is linked to an oligonucleotide that is complementary to a region of the selected RNA.

Preferred enzymes that can be conjugated to recognition reagents of the invention include, e.g., β-galactosidase, luciferase, horse radish peroxidase, and alkaline phosphatase. The chemiluminescent substrate for luciferase is luciferin. One embodiment of a chemiluminescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

Most typically, RNA expression is measured by quantitating the amount of label fixed to the solid support by binding of the recognition reagent. Typically, presence of a modulator during incubation will increase or decrease the amount of label fixed to the solid support relative to a control incubation which does not comprise the modulator, or as compared to a baseline established for a particular reaction type (e.g., presence of transcriptional activator). Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

I. Modulators

Essentially any chemical compound can be used as a potential modulator in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential therapeutic compounds (potential modulator compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random biooligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with $\beta$-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309–314 (1996) and PCT/US96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

As noted, the invention provides solid phase based in vitro assays in a high throughput format. Control reactions that measure the expression level of the selected RNA in a reaction that does not include a transcription modulator are optional, as the assays are highly uniform. Such optional control reactions are appropriate and increase the reliability of the assay. Accordingly, in a preferred embodiment, the methods of the invention include such a control reaction. For each of the assay formats described, "no modulator" control reactions which do not include a modulator provide a background level of expression from a given coding DNA.

In some assays it will be desirable to have positive controls to ensure that the components of the assays are working properly. At least two types of positive controls are appropriate. First, a known transcriptional activator (or other factor that increases RNA expression) can be incubated with one sample of the assay, and the resulting increase in transcription can be detected by measuring the resulting increase in RNA according to the methods herein. For example, Tat or a plasmid expressing Tat can expressed or added to the reaction with a Tat-inducible promoter operably linked to the nucleic acid encoding the selected RNA (e.g., an HIV LTR promoter) and expression of the encoded selected RNA monitored.

Second, a known inhibitor of transcription such as $\alpha$-amanitin (a strong inhibitor of the pol II transcription complex) can be added, and the resulting decrease in transcription similarly detected. It will be appreciated that modulators can also be combined with transcriptional activators or inhibitors to find modulators which inhibit transcriptional activation or transcriptional repression. As applied to the preceding two examples, an modulator that inhibits Tat is very valuable for its ability to repress HIV replication; accordingly, an assay for Tat modulators comprises adding Tat and a potential modulator to a reaction. Similarly, an inhibitor of $\alpha$-amanitin repression is very useful in counteracting the effects of $\alpha$-amanitin activation (e.g., due to wild mushroom poisoning); accordingly, an assay for $\alpha$-amanitin modulators comprises adding $\alpha$-amanitin and a potential modulator to a reaction.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (96) modulators. If 1536 well plates are used, then a single plate can easily assay from about 100—about 1500 different compounds. It is possible to assay several different plates per day; assay screens for up to about 6,000–20,000 different compounds is possible using the integrated systems of the invention.

J. Compositions, kits and integrated systems

The invention provides compositions, kits and integrated systems for practicing the assays described herein. For example, an assay composition having a reaction comprising a RNA duplex bound to recognition reagent, optionally an RNA expression or transcription modulator and a label bound to recognition reagent is provided by the present invention. Alternatively, the kit can comprise a reaction having an A-less or G-less RNA. As discussed above the duplex RNA typically comprises at least one and often several hybridized complementary nucleic acid oligonucleotides (DNA or RNA). Additional assay components as described above are also provided.

Solid substrates useful in the present invention include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The invention also provides kits for practicing the methods noted above. The kits can include any of the compositions noted above, and optionally further include additional components such as instructions to practice a high-throughput method of screening for an RNA expression or transcription modulator, one or more containers or compartments (e.g., to hold nucleic acids, reactions, modulators, or the like), a control activity modulator (e.g., α-amanitin which blocks pol II transcription), a robotic armature for mixing kit components or the like.

The invention also provides integrated systems for high throughput screening of potential modulators for an effect on RNA expression. The systems typically include a robotic armature which transfers fluid from a source to a destination, a controller which controls the robotic armature, a label detector, a data storage unit which records label detection, and an assay component such as a microtiter dish comprising a well having a recognition reagent affixed to the well, typically comprising a label (e.g., on the recognition reagent) detected by the label detector.

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art.

Any of the assays for compounds that modulate or mimic RNA expression levels as described herein, are amenable to high throughput screening. High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high thruput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or pentium chip—compatible DOS™, OS2™ WINDOWS™, WINDOWS NT™ or WINDOWS95™ based machines), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

III. Model in vitro assays using oligonucleotide protection and capture with anti-RNA:DNA antibodies The assays of the invention are further illustrated by consideration of the attached figures. These assays are provided by way of illustration and not by way of limitation; one of skill will recognize a variety of substitutions that can be made upon complete review of this disclosure.

Figure 5:
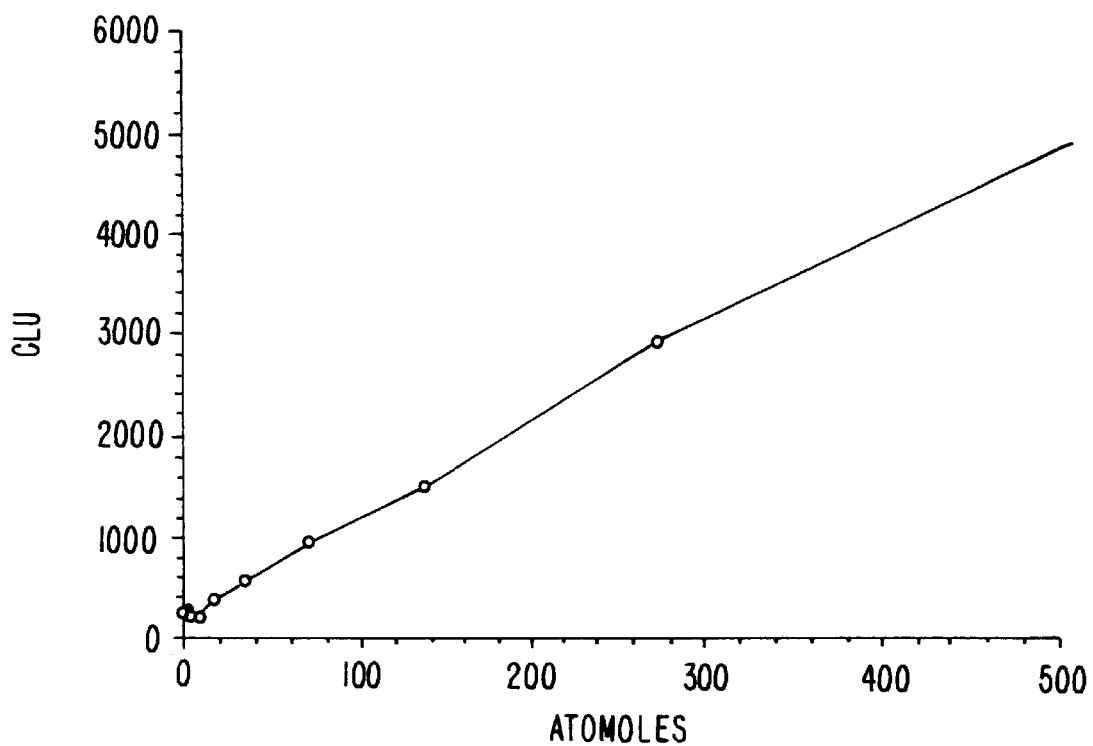
FIG. 5 shows a graph of sensitivity of mRNA detection using DNA:RNA antibody capture of Il-8 mRNA.
Figure 6:
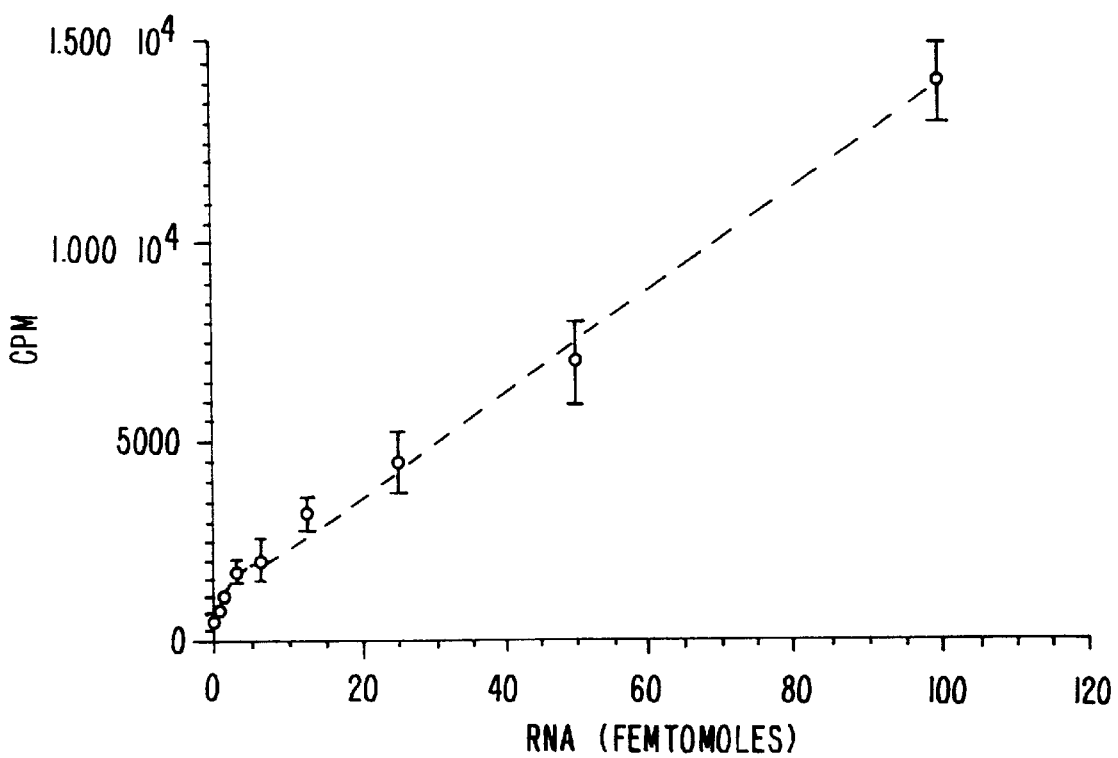
FIG. 6 shows a graph of sensitivity of mRNA detection using the sandwich hybridization capture methods.

FIG. 1 depicts a preferred exemplar assay of the invention. A transcription reaction is performed in the presence of anti-DNA:RNA antibodies immobilized to a solid substrate, e.g., a 96 well plate. These DNA:RNA antibodies function as the first recognition reagent. The transcription reaction contains a DNA construct with a promoter linked to a nucleic acid encoding a selected reporter RNA. The promoter optionally includes the Tar element from the HIV 5' LTR, which is recognized by the transcriptional includes activator Tat. Tat is optionally added to the transcription reaction along with potential Tat modulators. After incubation of the transcription reaction, oligonucleotides are added to the reaction, which are complementary to the reporter RNA. These oligonucleotide hybridize to the reporter RNA, creating an RNA:DNA hybrid. RNase A is then added to the reaction, which digests the single-stranded RNA. After proteinase K/SDS treatment, a second recognition reagent is added to the reaction, in the form of an anti-DNA:RNA antibody conjugated to alkaline phosphatase. After excess second unbound recognition reagent is removed from the plates by washing, the alkaline phosphatase substrate is added to the plate and the amount of reporter RNA affixed to the plate is detected by measuring chemiluminescence of the enzyme reaction. FIG. 5 shows that this assay has a sensitivity of approximately at least 10–50 atomoles of mRNA, using an Il-8 target mRNA.

IV. Model in vitro assays using G-less RNAs and RNase T1 digestion

Figure 2:
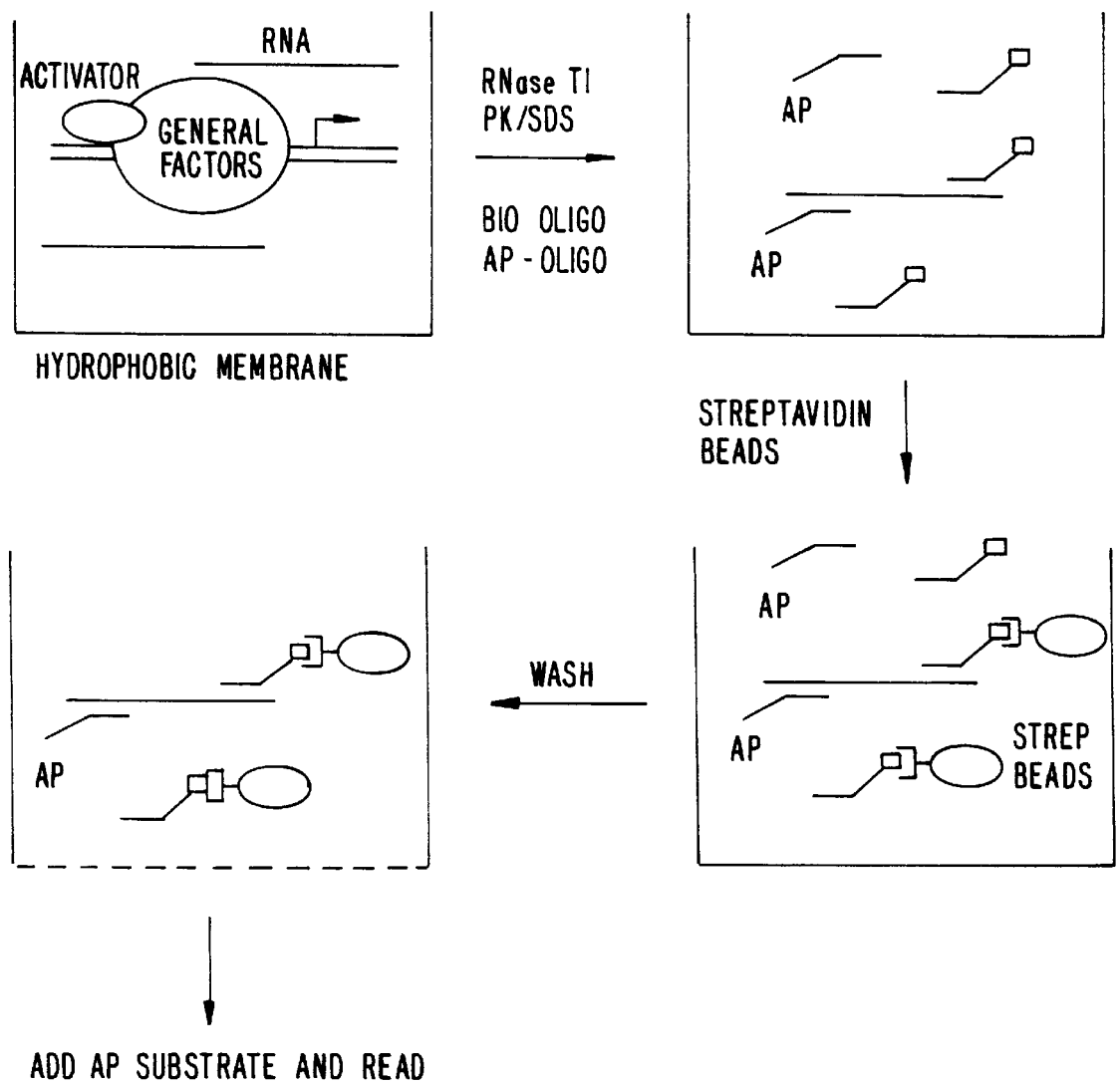
FIG. 2 is a drawing of a solid phase assay of the invention using a sandwich hybridization method with G-less transcripts to capture and detect the selected G-less RNA.
Figure 7:
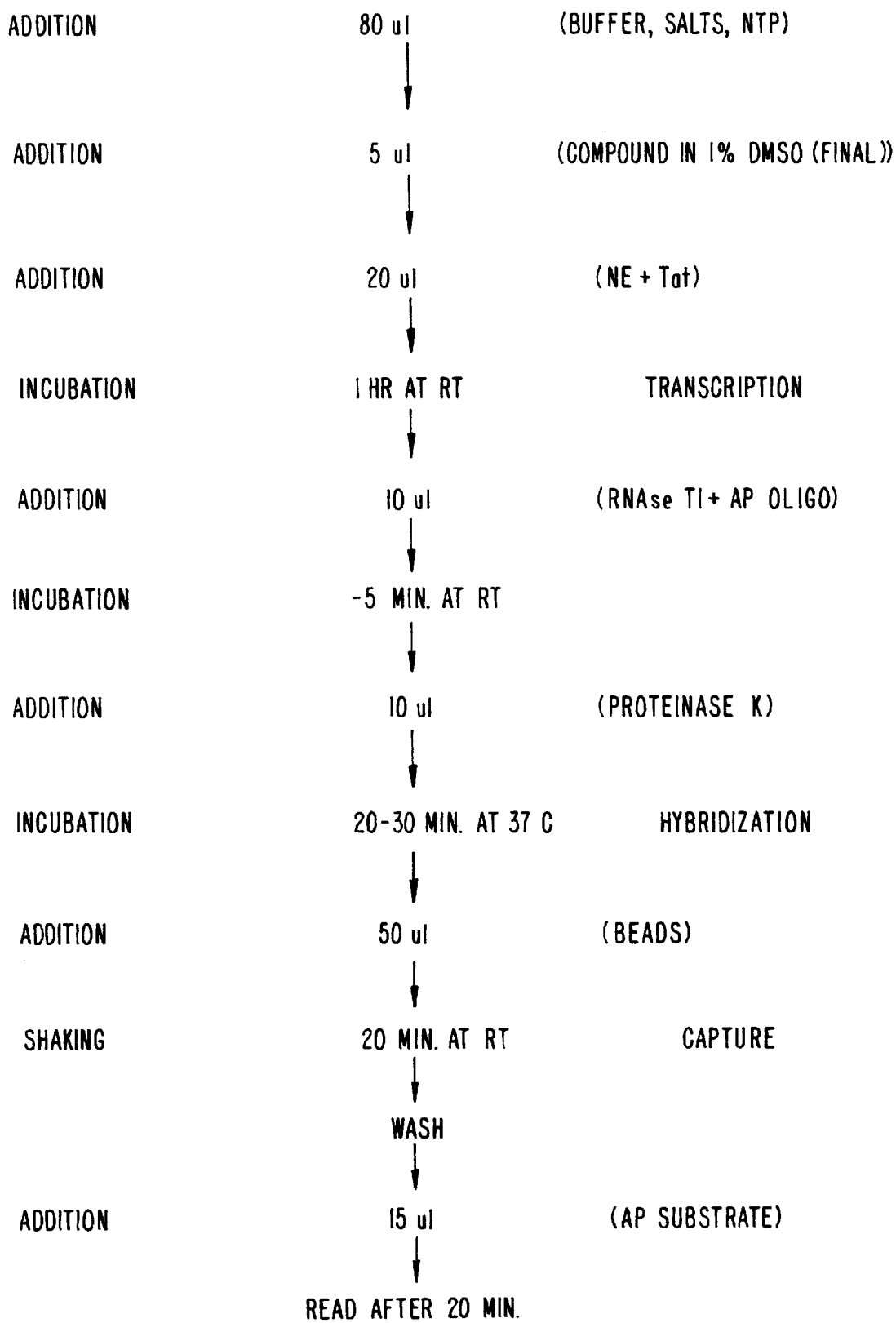
FIG. 7 shows a flowchart for an automated, high throughput sandwich assay for in vitro RNA detection.

FIGS. 2 and 7 depict a second preferred in vitro assay format. In this embodiment, a transcription reaction is performed using a G-less RNA as the reporter RNA. The transcription reaction contains a DNA construct with a promoter linked to a nucleic acid encoding the G-less RNA. The promoter optionally includes the Tar element from the HIV 5' LTR, which is recognized by the transcriptional activator Tat. Tat is optionally added to the transcription reaction along with potential Tat modulators. After incubation of the transcription reaction, RNase T1 is added to the reaction, which digests RNA at guanine positions. During or after the RNase digestion, a recognition reagent is added to the reaction, in the form of an oligonucleotide conjugated to biotin. Optionally, the RNase reaction can be performed in the presence of the biotinylated oligonucleotide (see FIG. 7). After the RNase digestion, protease K and SDS are added to the reaction. This step is important, as the proteinase K digestion increases the ability of the oligonucleotides to hybridize to the target RNA. Optionally, the labeled second recognition reagent is added with the proteinase K. Streptavidin beads are then added to the reaction, which bind to the biotinylated oligonucleotide and capture the G-less RNA on the beads. A second recognition reagent in the form of radioactively labeled oligonucleotides or an alkaline phosphatase linked enzyme are added to the reaction, which are complementary to the G-less reporter RNA. These oligonucleotide hybridize to the reporter RNA, acting as a detectable moiety. Excess unbound recognition reagent is removed by washing and shaking the beads on a glass fiber coated filter plate from Polyfiltronics (catalogue number UN35OPSW/PKP/M). The filter plate is also an important component of the reaction, as it must be resistant to the proteinase K/SDS digestion. The filter plate also allows appropriate washing of the beads and reduction of background. The amount of reporter RNA affixed to the beads is then detected by measuring radioactivity or by adding alkaline phosphatase substrate and determining chemiluminescence.

In a variation on this assay format, the sample is a lysed cells that have been previously contacted with a transcriptional activator and/or a transcription modulator. The cells are lysed with proteinase K and SDS, and then incubated with biotinylated olionucleotides that are complementary to the length of the RNA. The reaction is then digested with RNase A, and streptavidin beads are added to the reaction to capture the RNA, using the wash with the Polyfiltronic filter plate, as described above. Finally, the RNA is detected by contacting the reaction with a DNA:RNA antibody conjugated to alkaline phosphatase, and then adding a suitable alkaline phosphatase substrate for detection.

EXAMPLES

The following examples are provided by way of illustration only and not by way of limitation. Those of skill will readily recognize a variety of noncritical parameters, which are changed or modified to yield essentially similar results.

EXAMPLE I

High Throughput Assay for Detection of Tat Transcription Activator Modulators, Using Anti-RNA:DNA Antibody The following assay is used to examine Tat modulation of G-less mRNA expression in vitro. A potential activator or inhibitor compound is first added to the cell, followed by treatment with Tat transcription activator. The level of G-less mRNA expression is then assessed using an anti-RNA:DNA antibody, to determine the effect of the potential inhibitor or activator.

A. Reagents

1. Transcription buffers

BC100 Buffer

| Final concentration, 100 ml volume | Amount of stock solution |
|---|---|
| 20 mM Hepes pH 7.9 | 2 ml of 1M stock |
| 40% glycerol | 40 mL |
| 0.1 mM EDTA | 20 µL of 0.5M stock |
| 300 mM KCL | 10 mL of 3M stock |

Bring up to volume with milli-Q water and filter with 0.2 micron filter.

Transcription Buffer

20 µL BC100+β-mercaptoethanol (1 µL BME to 1 mL of 100 mL volume BC100 buffer)
4 µL 0.1M $MgCl_2$
5 µL 0.15 M sodium citrate (6 mM final conc.)
2 µL 1M Hepes, pH 7.9
0.5 µL DNA template LTRG #5 (2.7 µg/µL stock)
3.5 µL nucleotide mix
41 µL milli-Q water
76 µL total/well Nucleotide Mix (1 ml)

All nucleotides are 100 mM stock solution.

| | Final concentration | Source |
|---|---|---|
| ATP | 60 µL, 6 mM | BMB 27-2056-01 |
| GTP | 60 µL, 6 mM | BMB 27-2076-01 |
| UTP | 60 µL, 6 mM | BMB 27-2086-01 |
| CTP | 60 µL, 6 mM | BMB 27-2066-01 |
| 2M Tris pH 7.5 | 5 µL, 100 mM | |
| milli-Q water | 755 mL | |
| | 1000 µL total (200 µL aliquots stored at −80° C. freezer) | |

2. RNase T1—stock is 500,000 units/ml. Dilute ⅒ in H2O (Source: BMB 109207 diluted in milli-Q).

3. 10× Proteinase K buffer

| Final concentration | 10 ml volume |
|---|---|
| 100 mM Tris pH 7.5 | 0.5 ml 2M stock |
| 50 mM EDTA | 1.0 ml 0.56M stock |
| 2.5% SDS | 1.25 ml 20% stock |
| 10 mM $CaCl_2$ | 50 µL 2M stock |
| 1.4 mg/ml proteinase K | 0.9 ml of 15 mg/ml stock (source: BMB 1373-196) |

Bring up to 10 ml with autoclaved milli-Q water
Filter with 0.2 micron before adding the proteinase K.

4. α-amanitin
Make 0.1 mg/ml stock in MeOH. Dilute stock ⅒ (source: BMB 161 284).

5. Wash buffer
0.5× SSC
Calf Thymus DNA 0.02 mg/ml (Sigma Cat #D-8661)

B. Assay for in vitro transcription with capture by anti-RNA:DNA antibody

The following assay is used to measure transcription from a G-less cassette after addition of Tat (an HIV transcription activator) and optionally transcriptional activation or expression modulators.

75 µL of transcription buffer was added to the Digene antibody coated plate (anti-DNA:RNA antibody). 5 µl of α-amanitin (0.1 mg/ml stock) was added to a control. This is a known inhibitor of human polymerase II and will be the background level. 5 µL of potential modulator compound in 100% DMSO is added to the well. 0.5 µL TAT/well (70 nM final concentration)+20 µL/well of nuclear extract was premixed and added to the wells. A control well, which has no TAT, exhibits basal level transcript. The reaction was incubated for 1 hour at RT with shaking.

5–10 µL/well of RNase T1 was added to all wells. This enzyme cuts RNA at the G-sites, which leaves the G-less transcripts intact. The reaction was incubated for about 5 minutes at RT.

5 µL/well of 10× proteinase K+1.5 µL/well of G-less oligonucleotide were added to each well. G-less oligonucleotides are at a stock concentration of 1 pmole/µL. 10 oligonucleotides were used, and their sequences are given below. The reaction is incubated for 40 minutes at RT.

100 µL of Digene Detection Reagent I (pink in color) from Digene was added to the wells and incubated for 40 minutes at RT. The plates are washed 5× with Wash buffer.

Figure 3:
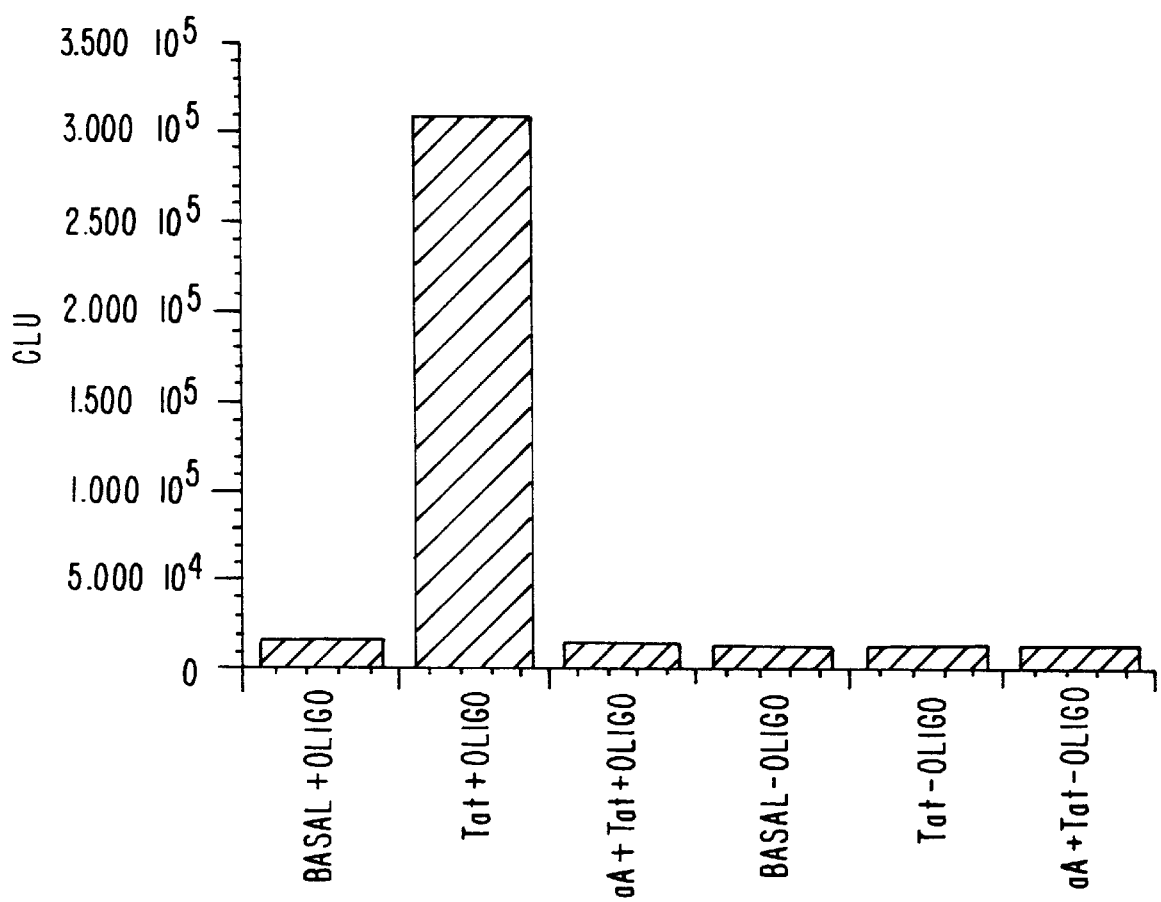
FIG. 3 shows Tat-induced in vitro transcription, detected using a DNA:RNA antibody.

Add alkaline phosphatase substrate CSPD was added to the wells (Detection reagent 2) from Digene and detected (see FIG. 3).

Sequence of G-less Oligonucleotides
GLESS1: 5'- GGA GTG GAA TGA GAA ATG AGT GTG AGG GGG (SEQ ID NO2)
GLESS2: 5'- GGA GAT AGA GGA GGG AGA GGT GAG GAG AGG ATA AGG ATA (SEQ ID NO:3)
GLESS3: 5'- TAT ATG AGA TGA GAT GAG TAG GGA GTA TTG GGT GAG TAG (SEQ ID NO:4)
GLESS4: 5'- GGG GTG ATA GGG ATG AGG ATG ATA GGG GGT ATG GAA GGA (SEQ ID NO:5)
GLESS5: 5'- GAA TAT AAT TGA GAT AAT TTT ATG ATT GGG GAT AAG ATT (SEQ ID NO:6)
GLESS6: 5'- GAA AGA GGG GAG GAA GGG GGG TGG AGG GGA TAT GGA AAG (SEQ ID NO:7)
GLESS7: 5'- GGA AAG GAG TAG AAT AGA ATG GGA GTG AAG GAA GAG GGG (SEQ ID NO:8)
GLESS8: 5'- GTG AGA GTG AAT GAT GAT AGA TTT GGG AAA TAT AGA AGA (SEQ ID NO:9)
GLESS9: 5'- AGG AGA AGA GAG GAG AAG ATA ATA GGA GGA ATA ATG AGG (SEQ ID NO:10)
GLESS10: 5'- AAA GGA GAG TAG GGT GGT ATA GAT GGA GGA AGG GTA TGG (SEQ ID NO:11)

EXAMPLE II

High Throughput Assay for Detection of Tat Transcription Activation Modulators, Using Radioactivity The following assay is used to examine Tat modulation of G-less mRNA expression in vitro. A potential activator or inhibitor compound is first added to the cell, followed by treatment with Tat transcription activator. The level of G-less mRNA expression is then assessed using a radioactively labeled oligonucleotide, to determine the effect of the potential inhibitor or activator.

A. Reagents

1. Transcription buffers

BC100 buffer

| Final concentration, 100 ml volume | Amount of stock solution |
| --- | --- |
| 20 mM Hepes pH 7.9 | 2 ml of 1M stock |
| 20% glycerol | 20 mL |
| 0.1 mM EDTA | 20 µL of 0.5M stock |
| 300 mM KCL | 10 mL of 3M stock |

Bring up to volume with milli-Q water and filter with 0.2 micron filter.

Transcription Buffer

20 µL BC100+β-mercaptoethanol (1 µL BME to 1 mL of 100 mL volume BC100 buffer)
6 µL 0.1M MgCl$_2$
4 µL 0.15 M sodium citrate (6 mM final conc.)
2 µL 1M Hepes, pH 7.9
0.22 µL DNA short template (0.7 µg/well) (PLG-6 #1, 3.2 µg/µL)
10 µL nucleotide mix
2.5 µL of 1 pmole/µL biotinylated oligonucleotide (5' Biotin TTG GGA AAT ATA GAA GAA GGA GAG A (SEQ ID NO:12) (Source: Cruachem Inc.)
36 µL milli-Q water
81 µL total/well
Nucleotide mix: see Example I.
2. RNase T1: see Example I.
3. 10× Proteinase K buffer: see Example I.
4. α-amanitin: see Example I.
5. γ-$^{33}$P labeled oligonucleotide—5' $^{33}$P GGG TGA GTA GGG GGT GAT AG (SEQ ID NO:13)

The 5× labelling mixture is:
30 µL milli-Q water
10 µL of 20 pmole/µL oligonucleotide (source: Cruachem Inc.)
10 µL 10× T4 kinase buffer (source: Promega)
50 µL γ-$^{33}$P ATP (100 µcurie, source: Dupont-NEN)
5 µL T4 kinase (T4 PNK PR-M410)
105 µL total
Labeling procedure:
a. Incubate in a 37° C. water bath for 1 hr. Add 2.5 µL of 0.5 M EDTA to stop the reaction. Bring the volume to 250 µL with 1× TE. Spin down any excess liquid off the sides of the eppendorf.
b. Purification of labeled oligonucleotide from unincorporated nucleotides:
QuickSpin column Preparation: At 30 min. into the labeling reaction, remove 2 Large Scale QuickSpin columns (Boehringer Mannheim #100 965). Invert several times to mix resin, then remove top cap, followed by bottom cap. Place column in collection tube and spin at 2,000 rpm, for 4 min.

Remove supernatant from collection tube and spin again at 2,000 rpm for 4 min. Replace the collection tube with fresh collection tube and store upright until ready to use.

Label the columns and tubes #1 and #2. Transfer the labelling reaction to column 1. Spin twice for 6 min. at 2000 rpm. Pipet liquid from tube 1 to column 2 and do two spins again at 2000 rpm for 6 minutes. Pipet liquid from tube 2 into a new eppendorf; typically about 200 µL is recovered.
c. Count 2 µL to check radioactivity; a typical yield is 2 million cpm/µL. Store at −20° C.
6. Wash buffer
1× PBS
10% isopropyl alcohol
0.4% NP-40
7. Bead buffer
5× SSC with 2.65 mg/ml calf thymus DNA
8. Bead preparation
Pipet the amount of beads needed for the total number of wells (20 µL stock beads×# of reaction wells). For every 1 ml of stock beads add 5 ml of 5× SSC buffer with ct DNA. Vortex and spin for 2 minutes at 2,000 rpm. Decant the buffer and replace with more 5× SSC/ct DNA. Repeat this two times. Finally suspend beads in 10× SSC plus ct DNA (# of wells×40 µL). 50 µL of beads are added to each well.
B. Assay for in vitro transcription of G-less cassette, using radioactivity The following assay is used to measure transcription from a G-less cassette after addition of Tat (an HIV transcription activator) and optionally transcriptional activation or expression modulators.

81 µL of transcription buffer was added to Polyfiltronics Uni-Filter glass fiber plate, catalogue number UN350PSW/ PKP/M. 10 µL of α-amanitin (0.1 mg/ml stock) was used in one transcription reaction as a negative control, as a known inhibitor of human polymerase II. 20 µL of HeLa cell nuclear extract was added to all the wells. 1 µL of TAT was added per well (70 nM final concentration) (the Tat and nuclear extract are typically premixed). Typically, one well lacks Tat, as a negative control for transcription activation. The α-amanitin well also lacks Tat. 1 µL of the potential modulator compound was added to the sample, e.g., 1 µL DMSO.

The reaction was incubated for 1 hour at RT with shaking. After the incubation period, 5 μL/well of RNase T1 was added to all wells. This enzyme cleaves RNA at guanine residues, leaving any reporter G-less transcripts intact.

6 μL of 10× Proteinase K was added to all wells. γ-$^{33}$P-labelled oligonucleotide was added to the wells, to give about 200,000 cpm/well to all the wells. The reaction was incubated for 40 minutes at 37° C.

50 μL of prewashed streptavidin coated beads was added to the reaction (source: BNM 1-529-188), and agitated for 20 minutes at RT, so as to keep the beads in suspension and not settled to the bottom.

The plates were washed using a Bio-Tek Instruments EL-403 auto washer, 5× with Wash buffer. Scintillation cocktail was added, and the samples were counted on a Packard TopCount.

Accordingly, the disclosures and descriptions herein are intended to be illustrative, but not limiting, of the scope of the invention which is set forth in the following claims. All patents and publications cited herein are incorporated in their entirety for all purposes, as though each were individually indicated to be incorporated by reference.

What is claimed is:

1. A method of measuring the expression of a selected RNA in the presence of a potential nucleic acid transcriptional activity modulator in a sample, the method comprising the steps of:
   (i) providing a sample comprising a potential transcriptional activity modulator and an expression cassette comprising a promoter operably linked to a selected nucleic acid encoding the selected RNA;
   (ii) incubating the sample with a DNA oligonucleotide, wherein a region of the oligonucleotide is complementary to a region of the selected RNA, forming an RNA:DNA heteroduplex;
   (iii) cleaving single-stranded RNA in the sample with an RNase enzyme;
   (iv) binding the RNA:DNA heteroduplex to a first recognition reagent comprising an antibody that binds to RNA:DNA heteroduplexes, the antibody immobilized on a solid substrate, thereby immobilizing the RNA:DNA heteroduplex on the solid substrate; and
   (v) detecting the RNA:DNA heteroduplex bound to the solid substrate.

2. The method of claim 1, wherein the sample further comprises a transcriptional activating molecule that induces transcription of the selected nucleic acid encoding the selected RNA.

3. The method of claim 1, the method comprising parallel repetition of steps (i)–(v) in a microtiter plate format.

4. The method of claim 1, wherein the RNA:DNA heteroduplex is detected by binding a second recognition reagent to the RNA:DNA heteroduplex, wherein the second recognition reagent is directly or indirectly detectable, and detecting the second recognition reagent.

5. The method of claim 4, further comprising removing unbound second recognition reagent by washing the unbound second recognition reagent from the solid substrate, wherein the unbound recognition reagent is not bound to the duplex.

6. The method of claim 4, wherein the second recognition reagent is an antibody that recognizes RNA:DNA heteroduplexes.

7. The method of claim 6, wherein the second recognition reagent comprises a detectable moiety.

8. The method of claim 1, wherein the RNA:DNA heteroduplex is detected by binding a second recognition reagent to the RNA:DNA heteroduplex, wherein the second recognition reagent is an antibody comprising an alkaline phosphatase label and the method further comprises adding an alkaline phosphatase substrate to the second recognition reagent.

9. The method of claim 1, wherein the solid support is selected from the group consisting of a bead, a membrane, and a 96-well plate.

10. The method of claim 1, wherein the single-stranded RNA is cleaved by contacting the single-stranded RNA with RNase A or RNase T1.

11. The method of claim 1, further comprising incubating the sample with a proteinase K.

12. The method of claim 1, further comprising incubating the sample with a chaotropic agent.

13. The method of claim 1, further comprising incubating the sample with a chaotropic agent and a protease.

14. The method of claim 1, wherein the step of detecting comprises detecting at least approximately 100–500 atomoles of selected RNA.

15. The method of claim 1, the method comprising repeating steps (i)–(v) in parallel in a microtiter plate format, wherein at least about 1,000 different potential activity modulators are tested for an effect on the level of expression of the selected RNA.

16. The method of claim 1, the method comprising repeating steps (i)–(v) in parallel in a microtiter plate format, wherein at least about 1,000 different potential activity modulators are tested for an effect on the level of expression of the selected RNA in one day.

17. The method of claim 1, the method comprising repeating steps (i)–(v) in parallel in a microtiter plate format, wherein between at least about 100 and at least about 6,000 different potential activity modulators are tested for an effect on the level of expression of the selected RNA in one day.

18. The method of claim 1, the method comprising repeating steps (i)–(v) in parallel in a microtiter plate format, wherein at least about 6,000 different potential activity modulators are tested for an effect on the level of expression of the selected RNA in one day.

19. A method of measuring expression of a selected RNA in the presence of a potential nucleic acid transcriptional activity modulator in a sample, the method comprising the steps of:
(i) incubating a sample comprising a potential transcriptional activity modulator and an expression cassette comprising a promoter operably linked to a selected nucleic acid encoding a selected G-less or a selected A-less RNA;
(ii) cleaving single-stranded RNA in the sample with an RNase enzyme that cleaves at guanine or adenine positions;
(iii) binding the selected RNA to a first recognition reagent directly or indirectly immobilized on a solid substrate, thereby immobilizing the selected RNA; and
(iv) detecting the level of expression of the selected RNA in the sample.

20. The method of claim 19, wherein the sample further comprises a transcriptional activating molecule that induces transcription of the selected nucleic acid encoding the selected RNA.

21. The method of claim 19, wherein the selected RNA is a G-less RNA and the single-stranded RNA is cleaved at guanine residues.

22. The method of claim 19, wherein the first recognition reagent is an oligonucleotide comprising a biotin molecule and the method comprises adding a streptavidin molecule attached to a solid support.

23. The method of claim 19, wherein the selected RNA is detected by binding a second recognition reagent to the selected RNA.

24. The method of claim 23, wherein the second recognition reagent is an oligonucleotide comprising a label.

25. The method of claim 24, wherein the label is a radioactive nucleotide.

26. The method of claim 24, wherein the label is an enzyme selected from the group consisting of horse radish peroxidase and alkaline phosphatase.

27. The method of claim 23, wherein the second recognition reagent is a DNA oligonucleotide comprising a label.

28. The method of claim 27, where the first recognition reagent is an antibody that binds RNA:DNA heteroduplexes, wherein the antibody is attached to a solid support.

29. The method of claim 19, wherein the single-stranded RNA is cleaved by contacted the single-stranded RNA with RNase T1 or RNase U2.

30. The method of claim 19, wherein the solid support is selected from the group consisting of a bead, a membrane, and a 96-well plate.

31. The method of claim 19, further comprising incubating the sample with a proteinase K.

32. The method of claim 19, further comprising incubating the sample with a chaotropic agent.

33. The method of claim 19, further comprising incubating the sample with a chaotropic agent and a protease.

34. The method of claim 19, wherein the step of detecting comprises detecting approximately at least 5–10 femtomoles of mRNA.

35. The method of claim 19, the method comprising repeating steps (i)–(iv) in parallel in a microtiter plate format, wherein at least about 1,000 different potential activity modulators are tested for an effect on the level of expression of the selected RNA.

36. The method of claim 19, the method comprising repeating steps (i)–(iv) in parallel in a microtiter plate format, wherein at least about 1,000 different potential activity modulators are tested for an effect on the level of expression of the selected RNA in one day.

37. The method of claim 19, the method comprising repeating steps (i)–(iv) in parallel in a microtiter plate format, wherein between at least about 100 and at least about 6,000 different potential activity modulators are tested for an effect on the level of expression of the selected RNA in one day.

38. The method of claim 19, the method comprising repeating steps (i)–(iv) in parallel in a microtiter plate format, wherein at least about 6,000 different potential activity modulators are tested for an effect on the level of expression of the selected RNA in one day.

* * * * *

```
                          SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 201 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly Pro Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly
            180                 185                 190

Gly Gly Gly Gly Gly Gly Gly Gly Gly
        195                 200

(2) INFORMATION FOR SEQ ID NO:2:

(i) SEQUENCE CHARACTERISTICS:
```

(A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

GGAGTGGAAT GAGAAATGAG TGTGAGGGGG                                             30

(2) INFORMATION FOR SEQ ID NO:3:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:3:

GGAGATAGAG GAGGGAGAGG TGAGGAGAGG ATAAGGATA                                   39

(2) INFORMATION FOR SEQ ID NO:4:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

TATATGAGAT GAGATGAGTA GGGAGTATTG GGTGAGTAG                                   39

(2) INFORMATION FOR SEQ ID NO:5:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

GGGGTGATAG GGATGAGGAT GATAGGGGGT ATGGAAGGA                                   39

(2) INFORMATION FOR SEQ ID NO:6:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

GAATATAATT GAGATAATTT TATGATTGGG GATAAGATT                                   39

(2) INFORMATION FOR SEQ ID NO:7:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

GAAAGAGGGG AGGAAGGGGG GTGGAGGGGA TATGGAAAG                                       39

(2) INFORMATION FOR SEQ ID NO:8:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

GGAAAGGAGT AGAATAGAAT GGGAGTGAAG GAAGAGGGG                                       39

(2) INFORMATION FOR SEQ ID NO:9:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

GTGAGAGTGA ATGATGATAG ATTTGGGAAA TATAGAAGA                                       39

(2) INFORMATION FOR SEQ ID NO:10:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

AGGAGAGAAG AGGAGAAGAT AATAGGAGGA ATAATGAGG                                       39

(2) INFORMATION FOR SEQ ID NO:11:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

AAAGGAGAGT AGGGTGGTAT AGATGGAGGA AGGGTATGG                                       39

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:

-continued

```
        (A) NAME/KEY: modified_base
        (B) LOCATION: 1
        (D) OTHER INFORMATION: /mod_base= OTHER
            /note= "N = biotinylated thymidine"

(xi) SEQUENCE DESCRIPTION: SEQ ID NO:12:

NTGGGAAATA TAGAAGAAGG AGAGA                                              25

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "G at position 1 contains
            gamma-33-P"

(xi) SEQUENCE DESCRIPTION: SEQ ID NO:13:

GGGTGAGTAG GGGGTGATAG                                                    20
```